United States Patent
Makino

(10) Patent No.: US 11,442,033 B2
(45) Date of Patent: Sep. 13, 2022

(54) SURFACE PROPERTY INSPECTION METHOD, SURFACE PROPERTY INSPECTION APPARATUS, AND SURFACE PROPERTY INSPECTION SYSTEM

(71) Applicant: SINTOKOGIO, LTD., Nagoya (JP)

(72) Inventor: Yoshiyasu Makino, Okazaki (JP)

(73) Assignee: SINTOKOGIO, LTD., Nagoya (JP)

( * ) Notice: Subject to any disclaimer, the term of this patent is extended or adjusted under 35 U.S.C. 154(b) by 254 days.

(21) Appl. No.: 16/628,525

(22) PCT Filed: Jun. 27, 2018

(86) PCT No.: PCT/JP2018/024356
§ 371 (c)(1),
(2) Date: Jan. 3, 2020

(87) PCT Pub. No.: WO2019/012991
PCT Pub. Date: Jan. 17, 2019

(65) Prior Publication Data
US 2020/0182814 A1 Jun. 11, 2020

(30) Foreign Application Priority Data
Jul. 10, 2017 (JP) .............................. JP2017-134382

(51) Int. Cl.
*G01N 27/02* (2006.01)
*G01N 33/204* (2019.01)

(52) U.S. Cl.
CPC .......... *G01N 27/023* (2013.01); *G01N 33/204* (2019.01)

(58) Field of Classification Search
CPC ..... G01N 27/02; G01N 27/023; G01N 27/026
(Continued)

(56) References Cited

U.S. PATENT DOCUMENTS 3,857,095 A * 12/1974 Mitchie .................. G01B 7/105
340/870.37
7,489,141 B1 * 2/2009 Vermeire ................. G01D 5/24
324/693
(Continued)

FOREIGN PATENT DOCUMENTS

CN 103119432 A * 5/2013 ............. G01B 7/105
CN 103649744 A * 3/2014 ............. G01B 7/105
(Continued)

OTHER PUBLICATIONS

MacKay et al., Using Impedance Measurements to Characterize Surface Modified with Gold Nanoparticles, Sensors—2017, 17, 2141; doi:10.3390/s17092141; www.mdpi.com/journal/sensors (Year: 2017).*

(Continued)

*Primary Examiner* — Patrick Assouad
*Assistant Examiner* — Sean Curtis
(74) *Attorney, Agent, or Firm* — Crowell & Moring LLP

(57) ABSTRACT

A surface property evaluation method includes a measurement step for acquiring the distribution of impedance in the depth direction of a test piece, and an evaluation step for evaluating the surface treatment state in the depth direction and wherein the evaluation step includes: a step for creating a reference measurement value group by preparing untreated sample, good sample, and sample to be evaluated, and calculating an impedance ratio $\gamma 1$ at each frequency for the untreated sample and good sample impedances; a step for creating an evaluation measurement value group by calculating an impedance ratio $\gamma 2$ for the impedances of untreated sample at each frequency relative to the sample to be evaluated impedances; and a step for evaluating the surface treatment state of a sample to be evaluated by comparing a (Continued)

reference measurement value group with the evaluation measurement value group.

12 Claims, 11 Drawing Sheets

(58) Field of Classification Search
USPC ... 324/71.1, 76.19, 600, 602, 605, 639, 650, 324/663
See application file for complete search history.

(56) References Cited

U.S. PATENT DOCUMENTS

| | | | | |
|---|---|---|---|---|
| 7,911,407 | B1 * | 3/2011 | Fong | H01Q 15/148 |
| | | | | 343/754 |
| 7,929,147 | B1 * | 4/2011 | Fong | H01Q 15/0046 |
| | | | | 343/909 |
| 7,982,457 | B2 * | 7/2011 | Redko | G01N 27/9046 |
| | | | | 324/754.21 |
| 9,157,892 | B2 * | 10/2015 | Makino | G01N 27/9046 |
| 9,733,231 | B2 * | 8/2017 | Reitsma | G01N 33/483 |
| 9,964,520 | B2 * | 5/2018 | Makino | G01N 27/90 |
| 10,048,227 | B2 * | 8/2018 | Makino | G01N 27/9046 |
| 10,338,055 | B2 * | 7/2019 | Reitsma | G01N 33/483 |
| 10,768,129 | B2 * | 9/2020 | Makino | G01N 27/72 |
| 10,768,144 | B2 * | 9/2020 | Makino | G01N 27/9046 |
| 11,066,805 | B2 * | 7/2021 | Li | G01H 15/00 |
| 2004/0212370 | A1 * | 10/2004 | Cunningham | G01N 27/026 |
| | | | | 324/693 |
| 2008/0211492 | A1 * | 9/2008 | Tsukada | G01R 33/063 |
| | | | | 324/234 |
| 2011/0006761 | A1 * | 1/2011 | Redko | G01N 27/9046 |
| | | | | 324/239 |
| 2014/0084910 | A1 * | 3/2014 | Makino | G01N 27/80 |
| | | | | 324/240 |
| 2016/0223483 | A1 * | 8/2016 | Reitsma | G01N 33/483 |
| 2017/0108470 | A1 * | 4/2017 | Makino | G01N 27/9006 |
| 2018/0188209 | A1 * | 7/2018 | Makino | C21D 11/00 |
| 2018/0299393 | A1 * | 10/2018 | Makino | G01N 27/023 |
| 2020/0182814 | A1 * | 6/2020 | Makino | G01N 33/204 |
| 2020/0386667 | A1 * | 12/2020 | Asada | G01N 27/26 |
| 2022/0163483 | A1 * | 5/2022 | Makino | G01N 27/9046 |

FOREIGN PATENT DOCUMENTS

| | | | | |
|---|---|---|---|---|
| CN | 103119432 | B * | 12/2015 | G01B 7/105 |
| CN | 103649744 | B * | 9/2016 | G01B 7/105 |
| CN | 107709981 | A * | 2/2018 | C21D 7/06 |
| CN | 107709982 | A * | 2/2018 | C21D 11/00 |
| CN | 110869756 | A * | 3/2020 | G01N 27/023 |
| CN | 111024782 | A * | 4/2020 | |
| DE | 102010010915 | A1 * | 9/2011 | G01B 7/06 |
| DE | 112014002603 | T5 * | 4/2016 | C21D 11/00 |
| EP | 3124964 | A1 * | 2/2017 | G01N 27/9033 |
| EP | 2707705 | B1 * | 7/2017 | G01B 7/105 |
| EP | 3299805 | A1 * | 3/2018 | C21D 11/00 |
| EP | 3299806 | A1 * | 3/2018 | C21D 7/06 |
| EP | 3654029 | A1 * | 5/2020 | G01N 27/023 |
| EP | 3299806 | B1 * | 11/2020 | C21D 7/06 |
| EP | 3748333 | A1 * | 12/2020 | G01N 17/02 |
| JP | H05-203503 | A | 8/1993 | |
| JP | 7-92140 | A | 4/1995 | |
| JP | 2009-64934 | A | 3/2009 | |
| JP | 2014066733 | A * | 4/2014 | G01B 7/105 |
| JP | 2015525336 | A * | 9/2015 | G01N 27/9046 |
| JP | 5850414 | B2 * | 2/2016 | G01B 7/105 |
| JP | 5877505 | B2 * | 3/2016 | C21D 11/00 |
| JP | 6052713 | B2 * | 12/2016 | G01B 7/06 |
| JP | 2017036918 | A * | 2/2017 | G01N 27/72 |
| JP | WO2015107725 | A1 * | 3/2017 | G01N 27/9086 |
| JP | WO2015125340 | A1 * | 3/2017 | G01N 27/72 |
| JP | 6176596 | B2 * | 8/2017 | B07C 5/344 |
| JP | 6181851 | B2 * | 8/2017 | G01N 27/9033 |
| JP | WO2016208382 | A1 * | 4/2018 | G01N 27/02 |
| JP | WO2017081879 | A1 * | 7/2018 | G01N 27/72 |
| JP | 6647682 | B2 * | 2/2020 | C21D 7/06 |
| JP | 6647683 | B2 * | 2/2020 | C21D 11/00 |
| JP | WO2019012991 | A1 * | 5/2020 | G01N 27/80 |
| JP | 2020144084 | A * | 9/2020 | G01N 27/80 |
| KR | 20180018814 | A * | 2/2018 | G01N 27/9046 |
| KR | 20180079284 | A * | 7/2018 | G01N 27/72 |
| KR | 20200020939 | A * | 2/2020 | G01N 27/80 |
| KR | 102159779 | B1 * | 9/2020 | G01N 27/9086 |
| WO | WO-9744659 | A1 * | 11/1997 | G01N 27/026 |
| WO | WO-2012153862 | A1 * | 11/2012 | G01B 7/105 |
| WO | WO-2015098234 | A1 * | 7/2015 | G01N 27/72 |
| WO | WO-2015107725 | A1 * | 7/2015 | G01B 7/06 |
| WO | WO-2015125340 | A1 * | 8/2015 | B07C 5/344 |
| WO | WO-2015145833 | A1 * | 10/2015 | G01N 27/9033 |
| WO | WO 2016/208382 | A1 | 12/2016 | |
| WO | WO-2016208382 | A1 * | 12/2016 | C21D 11/00 |
| WO | WO-2017081879 | A1 * | 5/2017 | C21D 7/06 |
| WO | WO-2019012991 | A1 * | 1/2019 | G01N 27/023 |
| WO | WO-2020183908 | A1 * | 9/2020 | G01N 27/80 |

OTHER PUBLICATIONS

Written Opinion in Application No. PCT/JP2018/024356, dated Nov. 11, 2018, 4 pages.

* cited by examiner

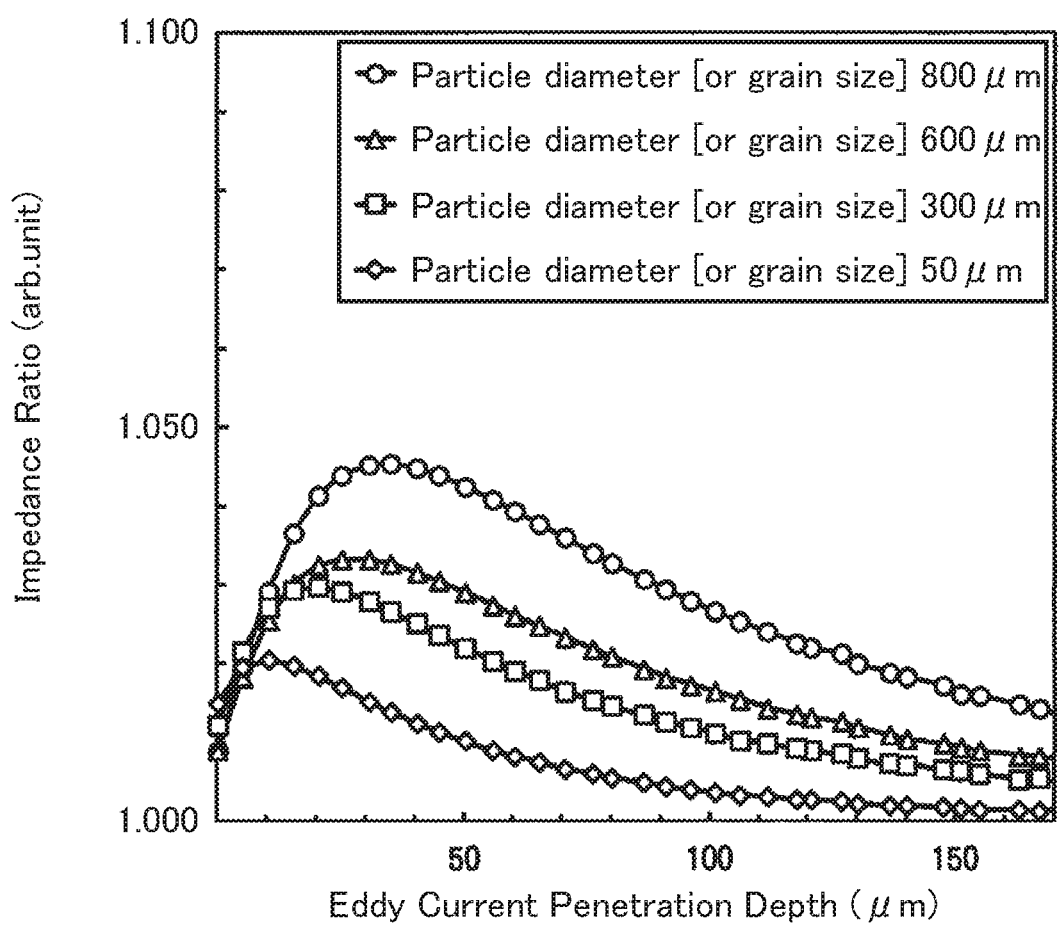

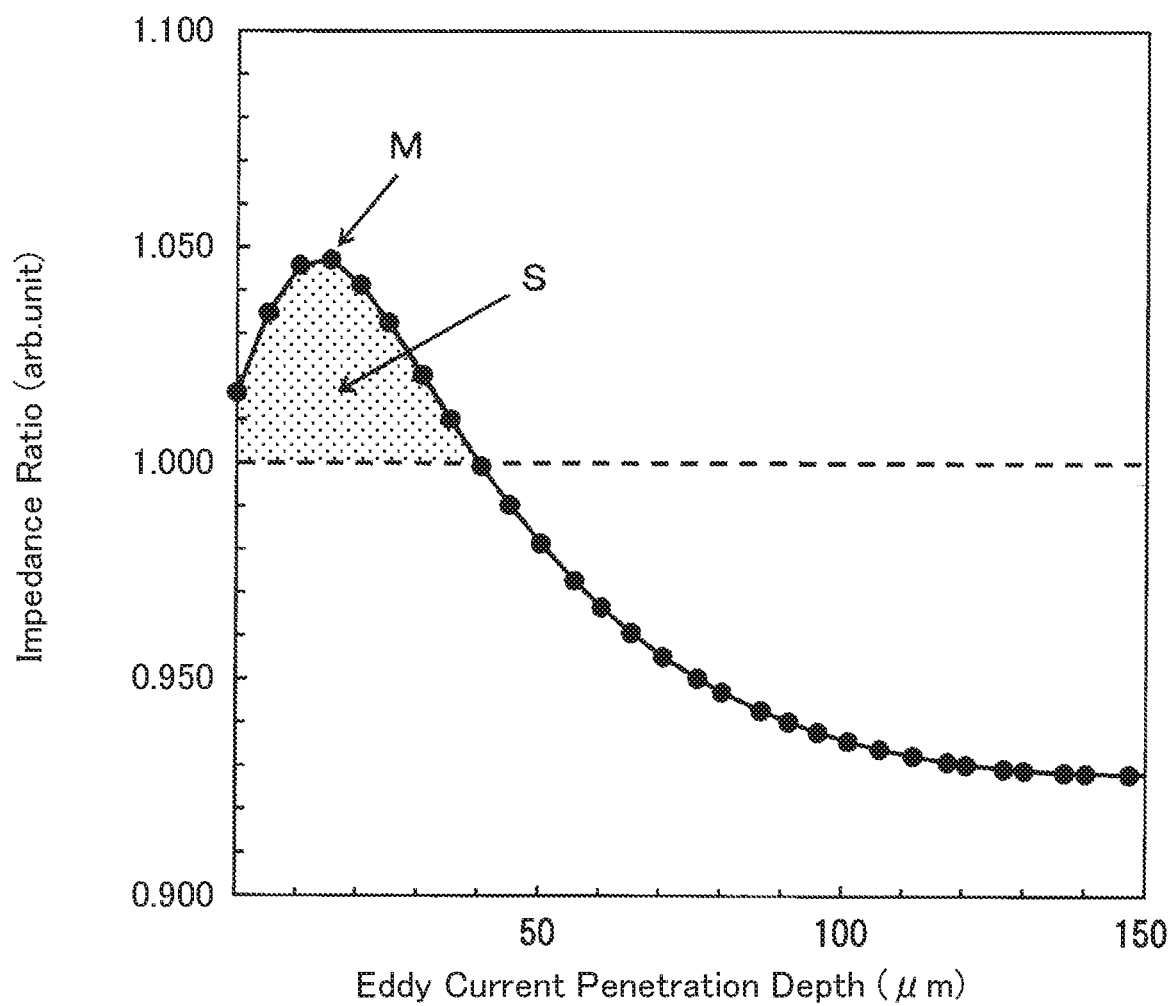

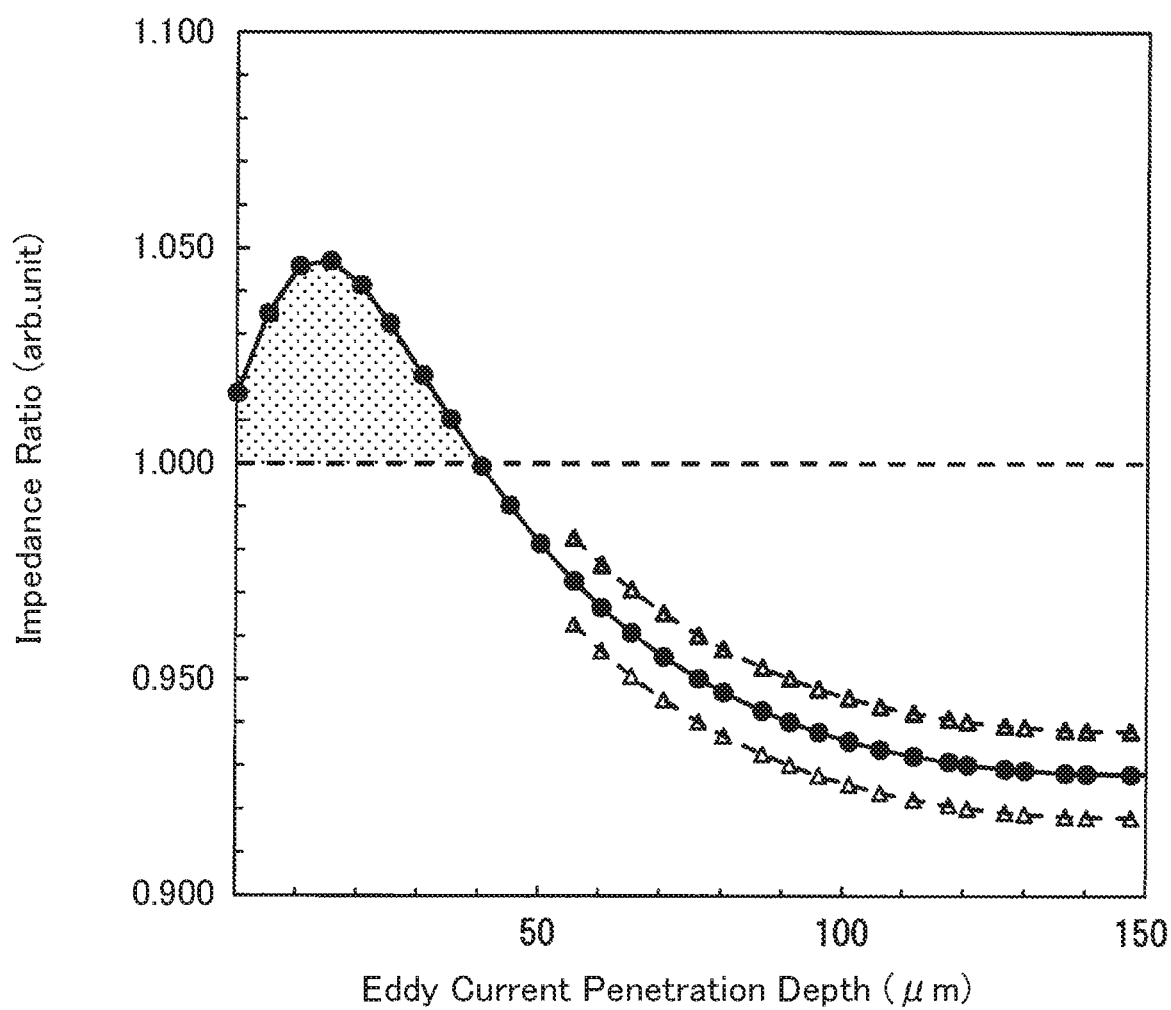

SURFACE PROPERTY INSPECTION METHOD, SURFACE PROPERTY INSPECTION APPARATUS, AND SURFACE PROPERTY INSPECTION SYSTEM

RELATED APPLICATIONS

This application is a 371 application of PCT/JP2018/024356 having an international filing date of Jun. 27, 2018, which claims priority to JP2017-134382 filed Jul. 10, 2017, the enter content of each of which is incorporated herein by reference.

TECHNICAL FIELD

The present invention pertains to a surface property evaluation method, surface property evaluation apparatus, and a surface property evaluation system for evaluating the state of surface treatment of a test piece such as a steel product to which surface treatment is applied.

BACKGROUND ART

Various heat treatments (carburization quenching, thermal nitriding, induction hardening, etc.) and a shot peening are broadly used as surface treatments for steel products and the like. Desired product characteristics can be improved by these surface treatments. For example, residual stress can be imparted by shot peening close to a product surface in order to improve fatigue strength. In surface treatment, consideration is given to process conditions so as to achieve a desired residual stress suited to a product's application. Precise evaluation of whether such surface treatments have been appropriately performed requires a grasp of the surface treatment state (e.g., the distribution of residual stress) in the depth direction relative to the product surface.

A method for measuring fatigue strength in steel is disclosed in Patent Document 1. In Patent Document 1, an evaluation is made of the depth at which the peak value is shown for compressive residual stress in steel subjected to shot peening as a surface treatment. However, the embodiment disclosed in Patent Document 1 requires setting measurement conditions for each different measurement subject or surface treatment condition. High accuracy evaluation is prevented due to variabilities such as those between individual pieces of steel material.

A different method for measuring fatigue strength in steel is disclosed in Patent Document 2. In Patent Document 2, the distribution of compressive residual stress in steel material is calculated by sequentially measuring the outer perimeter surface voltage value of a detection coil while sequentially changing the penetration depth of magnetic flux (magnetic permeability) of the steel material surface by sequentially changing the frequency of an excitation current sourced to an excitation coil brought into contact with the steel material. However, a voltage component caused by changes in magnetic permeability and a voltage component arising from the impedance of the detector coil itself are included in this detector coil output voltage value. The reliability of the measured values therefore declines when impedance characteristics of the detection coil itself change due to changes in the surrounding environment (temperature, noise, etc.). And while a design must account for the phenomenon of changes in detection signal caused by the distance between an excitation coil and the steel material in such a measurement apparatus, disclosure has not been made from this perspective. Thus the compressive residual strength of steel material cannot be accurately evaluated using the measurement apparatus of Patent Document 2.

PRIOR ART REFERENCES

Patent Documents

Patent Document 1: Japanese Published Unexamined Patent Application H07-09
Patent Document 2: Japanese Published Unexamined Patent Application H05-20
Patent Document 3: International Publication 2016/208382

SUMMARY OF THE INVENTION

Problems the Invention Seeks to Resolve

To solve the above problem, the applicants have developed a surface property evaluation apparatus and a surface property evaluation method using the same, capable of achieving precise evaluation by accounting for the distribution in the depth direction of residual stress in surface treated steel material based on a calculated impedance ratio, which is calculated by using a detector to cause an AC magnetism to penetrate a test piece and acquiring changes in impedance relative to frequency, then calculating a ratio (impedance ratio) between the impedance of an untreated sample and the impedance of a surface treated sample.

This enables accurate evaluation while accounting for distribution in the depth direction of residual stress in a surface treated steel material. However, the applicant, through diligent research, has discovered a surface property evaluation method for evaluating the state of surface treatment with even greater accuracy.

In addition, for products to which multiple surface treatments are applied, such as products which are shot peened after carburizing, there has also been a need to separately perform a pass/fail evaluation of surface treatment in each process step using a single measurement.

Thus the present invention has the object of providing a surface property evaluation method, a surface property evaluation apparatus, and a surface property evaluation system capable of accurate evaluation by accounting for the distribution in the depth direction of the surface treatment state of test pieces such as surface treated steel products. It further has the object of providing, in cases where multiple surface treatment steps are performed, a surface property evaluation method, a surface property evaluation apparatus, and a surface property evaluation system capable of making a pass/fail evaluation of the surface treatment state in each process step using a single measurement.

Means for Resolving Problem

In order to achieve the aforementioned object, the present invention uses a technical means as follows: a surface property evaluation method for evaluating surface treatment state of a metal product, comprising: a preparation step for preparing test pieces including a comparative sample whose surface is not treated, a reference good sample whose surface is appropriately treated, and a the test subject product for evaluation of performed surface treatment; an impedance distribution acquisition step for acquiring impedance distributions of the test pieces; and an impedance distribution analysis step for evaluating surface treatment state of the test subject product, based on the impedance distribution acquired in the impedance distribution acquisition step;

wherein the impedance distribution acquisition step comprises: a step for disposing the test piece inside a coil and applying an AC current to the coil to cause an AC magnetism excited by the coil to penetrate into the test piece; a step for varying the frequency of the AC current applied to the coil, thereby varying a penetration depth of the AC magnetism into the test piece; and a data acquisition step for acquiring the impedance distribution in a surface of the test piece by measuring coil impedances at multiple frequencies; wherein the impedance distribution analysis step comprises: a step for calculating an impedance ratio $\gamma 1$ ($Z_1/Z_0$) at each frequency, wherein the impedance ratio $\gamma 1$ of an impedance $Z_0$ of the comparative sample and an impedance $Z_1$ of the reference sample is acquired at each of the multiple frequencies in the data acquisition step to create a reference measurement value group $G\gamma 1$; a step for calculating at each frequency for the same multiple frequencies as in the reference measurement value group $G\gamma 1$ an impedance ratio $\gamma 2$ ($Z_2/Z_0$), wherein the impedance ratio $\gamma 2$ of an impedance $Z_2$ of the test subject product and the impedance $Z_0$ of the comparative sample is acquired in the data acquisition step, to create an evaluation measurement value group $G\gamma 2$; and a step for evaluating the surface treatment state of the test subject product by comparing certain evaluation criteria, set based on the reference measurement value group $G\gamma 1$, with the evaluation measurement value group $G\gamma 2$; wherein the evaluation criteria are selected from among: an area width criterion in which the surface treatment state of the test subject product evaluated by setting an allowable impedance ratio range at each frequency based on the impedance ratio $\gamma 1$ at each frequency of the reference measurement value group $G\gamma 1$ and comparing said allowable impedance ratio range to the impedance ratio $\gamma 2$; a peak criterion in which the surface treatment state of the test subject product is evaluated by setting an allowable peak position range based on the peak position of the reference measurement value group $G\gamma 1$ relative to frequency and comparing said allowable peak position range to the peak position in the impedance ratio $\gamma 2$; and an integral area criterion in which the surface treatment state of the test product is evaluated by setting an allowable integral value range based on the integral value of the impedance ratio $\gamma 1$ of the reference measurement value group $G\gamma 1$ in a predetermined frequency range, and comparing said allowable integral value range to the integral value of the impedance ratio $\gamma 2$ in said frequency range.

In the invention thus constituted, the surface property evaluation method for evaluating the surface treatment state of a surface treated test piece comprises: a data acquisition step for acquiring the distribution of impedances in the test piece depth direction, and an impedance distribution analysis step for evaluating the surface treatment state in the depth direction of a test piece based on the impedance obtained in the data acquisition step; an evaluation of the surface treatment state with consideration of the depth direction from the surface of the test subject product can be performed by comparing a reference measurement value group $G\gamma 1$, which calculates the impedance ratio $\gamma 1$ at each frequency for the impedance of the comparative sample and the reference sample at multiple frequencies in the impedance distribution analysis step, to an evaluation measurement value group $G\gamma 2$, which calculates an impedance ratio $\gamma 1$ between the impedance of the test subject product at the same frequencies as for reference measurement value group $G\gamma 1$ and the impedance of the comparative sample T1 at each frequency. Evaluation is performed by selecting from among area, peak, and integral area as evaluation criteria, thereby enabling a higher accuracy evaluation.

The present invention preferably uses a technical means whereby the impedance distribution analysis step comprises a step for calculating the penetration of the AC magnetism into the test subject product based on the frequency of AC current applied to the coil, and the surface treatment state is evaluated by respectively producing a reference 2D map displaying the impedance ratio $\gamma 1$ relative to depth from the surface for the reference sample based on the reference measurement value group $G\gamma 1$, and an evaluation 2D map displaying the impedance ratio $\gamma 2$ relative to depth from the surface of the test subject product based on the evaluation measurement value group $G\gamma 2$.

In the invention thus constituted, a reference 2D map and an evaluation 2D map can be compared, making it easier to visually grasp a surface treatment state in the depth direction, such as pass/fail of evaluation results, the degree thereof, and so forth.

In the present invention, preferably, a technical means is used wherein, in the impedance distribution analysis step, when evaluating the surface treatment state of the test subject product to which multiple surface treatments have been applied, different evaluation criteria are selected according to the depth from the surface of the test subject product.

Since the factors affecting impedance and the depth affecting surface treatments vary depending on the surface treatment step, the tendency of the impact in the depth direction of the impedance ratio between the comparative sample and surface treated product differs between surface treatment steps. In the invention thus constituted, by selecting different evaluation criteria based on the depth from the surface of the test subject product, an evaluation can be performed by a separate pass/fail evaluation of the surface treatment state for each manufacturing step by performing just one evaluation of the test subject product.

In the present invention, preferably, a technical means is used whereby when the surface treatment applied to the test subject product includes shot peening, the peak criterion or the integral area criterion is selected to evaluate the surface treatment close to the surface of the test subject product.

When surface treatment includes shot peening, the evaluation measurement value group and the evaluation 2D map exhibit a behavior unique to shot peening, therefore a peak criterion or integral area criterion suited to evaluating that behavior is preferably selected, as in the present invention constituted as described above.

In the present invention, preferably, a technical means is used wherein a surface treatment state resulting from shot peening is evaluated.

In the invention thus constituted, a pass/fail evaluation of shot peening can be made based on evaluation results from a peak criterion or integral area criterion.

In the present invention, preferably, a technical means is used wherein the allowable ranges for the area width criterion, the peak criterion, and the integral area criterion are set based on the variability of multiple reference measurement value groups $G\gamma 1$.

In the invention thus constituted, the allowable ranges for evaluation criteria are set based on the variability in multiple reference measurement value groups $G\gamma 1$, therefore statistically appropriate allowable ranges can be set according to quality control range limits, and evaluation accuracy of the surface treatment state can be improved.

The present invention is a surface property evaluation apparatus for evaluating surface treatment of a metal product comprising: an oscillator comprising an AC power supply and a variable frequency circuit capable of varying a frequency of AC current output by the AC power supply; a detector connected to the oscillator, comprising a coil for exciting AC magnetism by the AC current applied from the variable frequency circuit, for causing the AC magnetism to penetrate each of test pieces wherein the test pieces include a comparative sample whose surface is not treated, a reference sample whose surface is appropriately treated, and a test subject product for evaluation of performed surface treatment; a measurement instrument, connected to the variable frequency circuit and the detector, for acquiring an impedance distribution for each test piece; and an evaluation device that evaluates the surface treatment state of the test subject product based on the impedance distribution acquired for the test subject product.

In the surface property evaluation apparatus of the invention thus constituted, the surface property evaluation apparatus of the invention can be favorably practiced.

Also, the present invention is a surface property evaluation system using a technical means constituted by the surface property evaluation apparatus of the present invention and one or multiple surface treatment apparatuses connected to the surface property evaluation apparatus; whereby the surface property evaluation apparatus is capable of transmitting evaluation results for the surface treatment state of the test subject product to a selected surface treatment apparatus.

In the invention thus constituted, a surface property evaluation system can be connected or built into a surface treatment apparatus to constitute a surface treatment evaluation system for transmitting evaluation results regarding the surface treatment state of the test subject product.

In the invention, preferably, the surface property evaluation apparatus uses a technical means wherein the surface property evaluation apparatus is configured to control the selected surface treatment apparatus.

In the invention thus constituted, a surface treatment apparatus can be controlled based on the results of the surface treatment state evaluation for the test subject product.

In the present invention, preferably, the surface property evaluation apparatus uses a technical means whereby a determination is made as to which of multiple surface treatment apparatuses used to apply surface treatment to test subject product produced an anomalous surface treatment caused by the surface treatment apparatus.

In the invention thus constituted it is possible, using the surface property evaluation apparatus, to determine which surface treatment apparatus among the multiple surface treatment apparatuses performed the surface treatment step in which an anomaly was found.

The present invention is a surface property evaluation system comprising a surface property evaluation apparatus, and uses a technical means whereby the surface property evaluation apparatus is configured to record evaluation results for the surface treatment state of the test subject product.

In the invention thus constituted, evaluation records can be recorded, therefore various analyses, measurement value corrections to the surface property evaluation apparatus, and corrections to processing conditions in previous and subsequent steps and the like can be performed based on these records.

The present invention uses a technical means which preferably further comprises one or multiple surface treatment apparatuses connected to the surface treatment evaluation apparatus, whereby the surface treatment evaluation apparatus is configured to record surface treatment conditions for a surface treatment apparatus used to surface treat the test subject product, in association with evaluation results for the test subject product.

In the invention thus constituted, a surface treatment history relative to each test subject product is recorded, thus enabling higher reliability products to be manufactured.

BRIEF DESCRIPTION OF FIGURES

FIG. 7: An explanatory diagram showing changes in impedance ratio based on the diameter of shot used in shot peening.

FIG. 8: A diagram explaining a method for evaluating the surface treatment state of the test subject product using a peak criterion in the determination step.

FIG. 9: An explanatory diagram of the test subject product surface treatment state evaluation method of the test subject product combining an area width criterion and an integral area criterion.

EMBODIMENTS OF THE INVENTION (Surface Property Evaluation Apparatus)

We explain the surface property evaluation apparatus of the present invention with reference to figures. Note that the up, down, left, and right directions in the explanation below indicate directions in the diagram unless otherwise noted.

Figure 1:
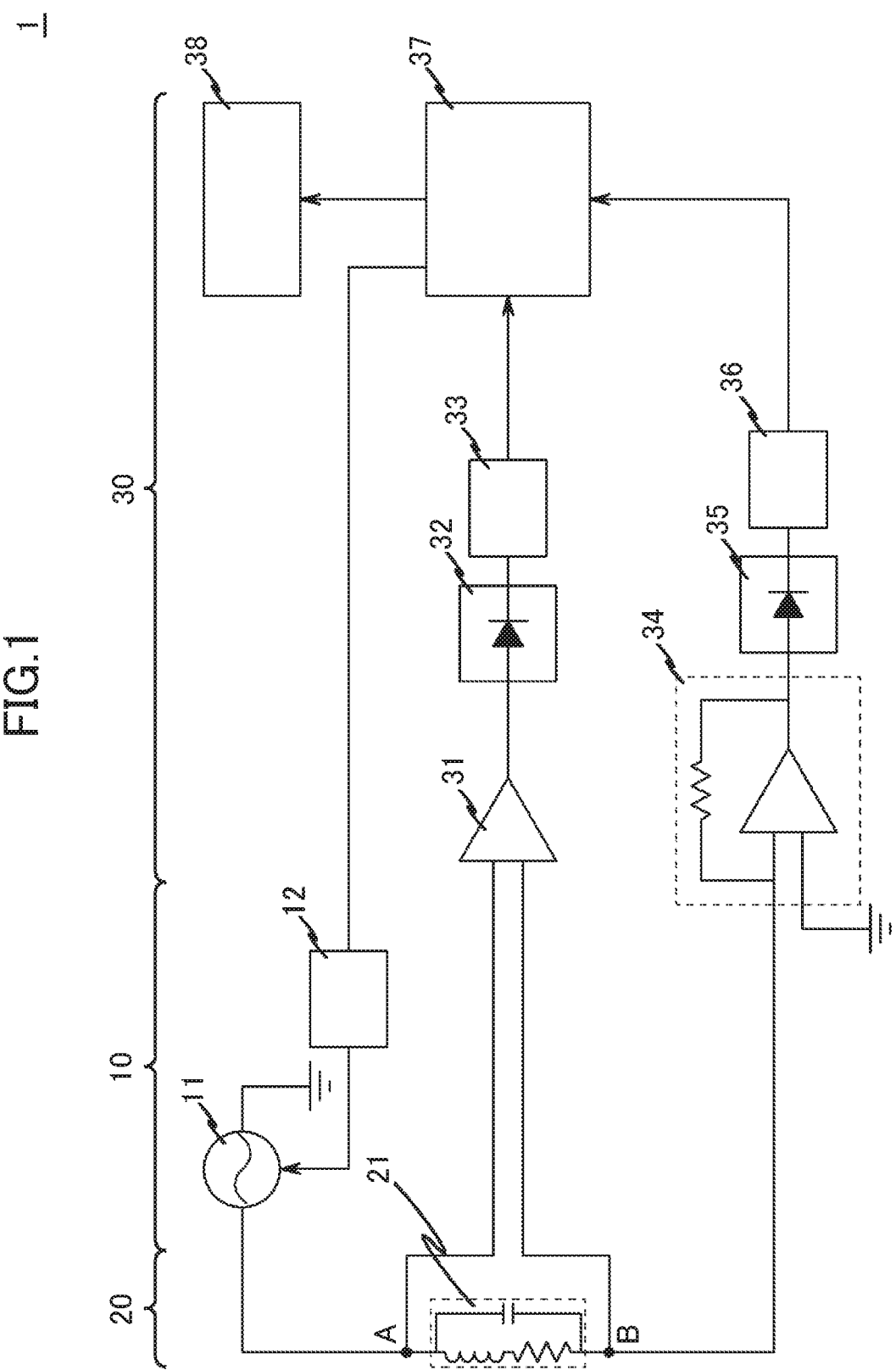
FIG. 1: A circuit diagram showing the constitution of a surface property evaluation apparatus.

As shown in FIG. 1, the surface property evaluation apparatus 1 of the present invention comprises an oscillator 10, a detector 20, and a measurement instrument 30.

The oscillator 10 comprises an AC power supply 11 and a variable frequency circuit 12. The variable frequency circuit 12 is connected to the AC power supply 11, and can change the frequency of AC current output from the AC power supply 11.

Figure 2:
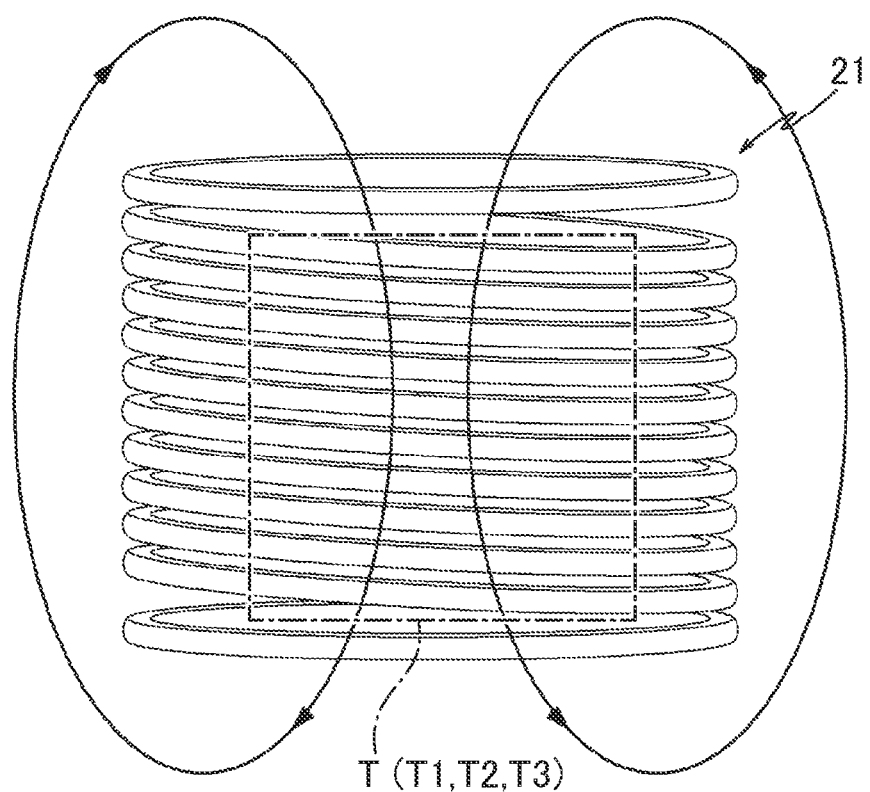
FIG. 2: An explanatory diagram schematically showing the AC magnetism (magnetic flux) produced in a coil.

The detector 20 includes the coil 21 shown in FIG. 2. One end (point A) of the coil 21 is connected to the AC power supply 11, supplying AC current output from the AC power supply 11. Details of the coil 21 are discussed below. Included inside the coil 21 is one of test pieces T which consist of a comparative sample T1 whose surface is not treated, a reference sample T2 whose surface is appropriately treated, and a test subject product T3 for evaluation of performed surface treatment.

The measurement instrument 30 comprises an amplifying circuit 31, an absolute value circuit 32, a low pass filter (LPF) 33, an I/V conversion circuit 34, an absolute value circuit 35, a LPF36, a control means 37, and a display device 38. The control means 37 comprises an evaluation means for evaluating the state of a test piece T using the evaluation method described below. Also, a memory means is provided within the control means 37 or in an area not shown.

The amplifying circuit 31 is connected to points A and B on the two terminals of the coil 21. An electrical potential difference signal between point A and point B is input to the amplifying circuit 31 and amplified. This amplified signal is full-wave rectified by the absolute value circuit 32 and converted to DC by the LPF 33. This converted signal is input to the control means 37.

The IN conversion circuit 34 is connected to the other terminal side (point B) of the coil 21. A signal indicating the current value of current flowing in the coil 21 is input to the IN conversion circuit 34 and converted to a signal indicating a potential difference. After full-wave rectification by the absolute value circuit 35, the signal is converted to DC by LPF36. This converted signal is input to the control means 37.

The control means 37 is connected to the variable frequency circuit 12, the LPF33, and the LPF36, and the frequency of AC current applied to this coil as well as a signal passed through the LPF33 and the LPF36 relative to this frequency are respectively input thereto. Computation is performed based on these input signals, and an evaluation of a test subject product T3 is made based on those computed results. Note that changes in frequency of the AC current may also be made manually, or the frequency may be automatically changed by providing the ability for a signal which continuously changes the frequency to be output by the variable frequency circuit 12 to the control means 37. In the present embodiment, the latter was adopted.

The display device 38 displays or issues warning of evaluation results by the control means 37.

We next explain the coil 21. The coil 21 is formed in a cylindrical shape by winding conductive wire. A single conductor wire, or one formed as a single wire by binding together multiple fine conductors, may be used for this wire. In the latter case, the multiple fine conductive wires may be formed by twisting together, or may be formed into a single wire by interweaving multiple fine conductive wires. It is also possible to form a single fine wire by twisting after multiple fine conductive wires are interwoven into a single wire. By using multiple fine conductor wires bound together as if into a single wire as the wire material for the coil 21, the resonant frequency of the coil 21 (itself) can be raised.

The coil 21 may have a structure in which wire is wound onto a hollow cylindrical core (a core coil), but in this embodiment we chose a structure without a core (an air core coil).

By causing AC magnetism excited by application of an AC current to the coil 21 to permeate a test piece T, eddy currents are generated in the test piece T. Eddy currents produce a diamagnetic field relative to the AC magnetism, and the depth of permeation of the AC magnetism varies. The size of the magnetic flux combining this diamagnetic field and AC magnetism differs depending on the degree of residual stress, which indicates the extent of surface treatment. Therefore evaluating the electrical properties of current flowing in the coil 21 enables an evaluation of the degree of surface treatment. In this case, an accurate evaluation of the surface properties of the test piece T requires a more accurate grasp of the diamagnetic field. Therefore, in the coil 21 of the present embodiment, the number of wire windings was adjusted so that the resonant frequency was at or above the working frequency bandwidth. The depth (influence layer) from the surface modified by the surface treatment is approximately 10 to 1000 μm. In this case, assuming a working frequency bandwidth of $0.5 \times 10^3$ Hz to $20 \times 10^6$ H, the resonant frequency of the coil 21 may be set to 10 MHz or greater (preferably at least twice the working frequency band). Also, the affected layer when shot peening is selected as the surface treatment is approximately 10 to 300 μm, therefore assuming a working frequency band of $1 \times 10^3$ Hz to $2 \times 10^6$ Hz, the coil 21 resonant frequency may be set to 10 MHz or greater (preferably at least twice the working frequency band).

It is desirable if possible to bring the coil 21 into close proximity with the test piece T so that AC magnetism excited in the coil 21 permeates into the test piece T; there is no particular limitation as to the shape of the detector 20. A structure was adopted whereby the detector 20 of the present embodiment is given a cylindrical shape, and the test piece T is inserted into the interior thereof. I.e., inserting a test piece T into the center portion of the coil allows the coil 21 to envelope the perimeter surface of a test piece T. In this structure, material-caused variability in the direction perpendicular to the depth direction within the test piece T can be reduced, improving evaluation accuracy. Also, eddy currents can be made to permeate the side perimeter surface of the test piece T, which is to say the entire surface subject to evaluation, so that the entirety of the surface being evaluated can be evaluated in a single measurement iteration.

Since the test piece T is surrounded by the coil 21, the influence of local states on the test piece T is small. For example, a more accurate surface property evaluation can be done by performing a microdestructive test (stress measurement, X-ray measurement, etc.) by using electrolytic polishing and comparing actual residual stress measurements with result of the surface treatment state evaluation.

(Surface Property Evaluation Method)

We next explain a method for evaluating the surface property state and the surface treatment process for a test piece T. Below we explain an example in which an evaluation is made of the surface treatment state and the surface treatment process for a test piece T on which the surface treatment is shot peening ("SP" below) following carburization.

The surface property evaluation method of the invention is made up of a preparation step, an impedance distribution acquisition step, and an impedance distribution analysis step.

First, in the preparation step, a comparative sample T1 whose surface is not treated, a reference sample T2 whose surface is appropriately treated, and a test subject product T3 for evaluation of performed surface treatment.

Next, the impedance distribution acquisition step includes a step for penetrating AC magnetism into the interior of a test piece T, a step for varying the penetration depth of the AC magnetism, and a data acquisition step for acquiring the impedance distribution.

In the step for penetrating AC magnetism into the interior of the test piece T, the test piece T is first placed inside the coil 21 of the detector 20, and the AC magnetism is made to penetrate the test piece T by applying AC current to the coil 21. Note that so long as this AC magnetism continues to penetrate into the interior of the test piece T when the AC magnetism is excited in the coil 21, there are no particular limitations as to the method of placement of the test piece T. In this embodiment, the comparative sample T1 is placed at the center of the round cross section of the coil 21, so that the entire test piece T is positioned on the interior of the coil 21. By this placement of the test piece T, variability caused by materials can be reduced in the direction perpendicular to the depth direction of the test piece T interior, therefore measurement accuracy can be increased.

Next, as a step for varying the penetrating depth of AC magnetism, a signal controlling the frequency of the AC magnetism output from the AC power supply 11 is output from the control means 37 to the variable frequency circuit 12 to cause the AC power supply 11 to operate. Operation of the AC power supply 11 excites AC magnetism in the coil 21 (FIG. 2). A test piece T is placed on the inner perimeter side of the coil 21 so that this AC magnetism penetrates the test piece T. Eddy currents are generated in the test piece T by the penetration of the AC magnetism. The eddy current produces a diamagnetic field relative to the AC magnetism. At this point, the magnetic permeability changes depending on the degree of residual stress. Therefore the size of the magnetic flux combining this diamagnetic field and AC magnetism differs depending on the degree of residual stress, which indicates the extent of surface treatment. In other words, the signal indicating the electric characteristics of the coil when an AC current is flowing therein (the signal indicating the potential difference between the coils (between A and B) and the signal indicating the current value after flowing through the coil) changes depending on the degree of residual stress. Impedance $Z_0$ at a particular frequency is calculated by the control means 37 from the signal passing through the amplifying circuit 31-absolute value circuit 32-LPF33 and input into the control means 37, and from the signal passing through I/V conversion circuit 34-absolute value circuit 35-LPF36 and input into the control means 37.

Here, the depth of penetration of AC magnetism into the test piece T depends on the frequency of the AC current. As the frequency of the AC current output from the AC power supply 11 is varied, the impedance $Z_0$ of the coil 21 is calculated from these signals for each frequency and stored in a memory means. I.e., in the data acquisition step, the penetration depth of AC magnetism into the test piece T is varied with multiple corresponding frequencies and the impedance of the coil 21 is measured for multiple frequencies to obtain a distribution of impedances in the depth direction of the test piece T.

The same operation is performed on reference samples T2 and test subject products T3 to obtain their respective distribution of impedances $Z_1$, $Z_2$ in the depth direction. Here, the AC current frequency shall be the same frequencies as the frequencies in the comparative sample T1.

Next, the impedance distribution analysis step includes a step for creating a reference measurement value group Gγ1, a step for creating an evaluation measurement value group Gγ2, and a step for evaluating the surface treatment state of the test subject product T3. That is, in the impedance distribution analysis step, the surface treatment state in the depth direction of the test piece T is evaluated based on the impedance distribution obtained in the impedance distribution acquisition step.

Figure 3:
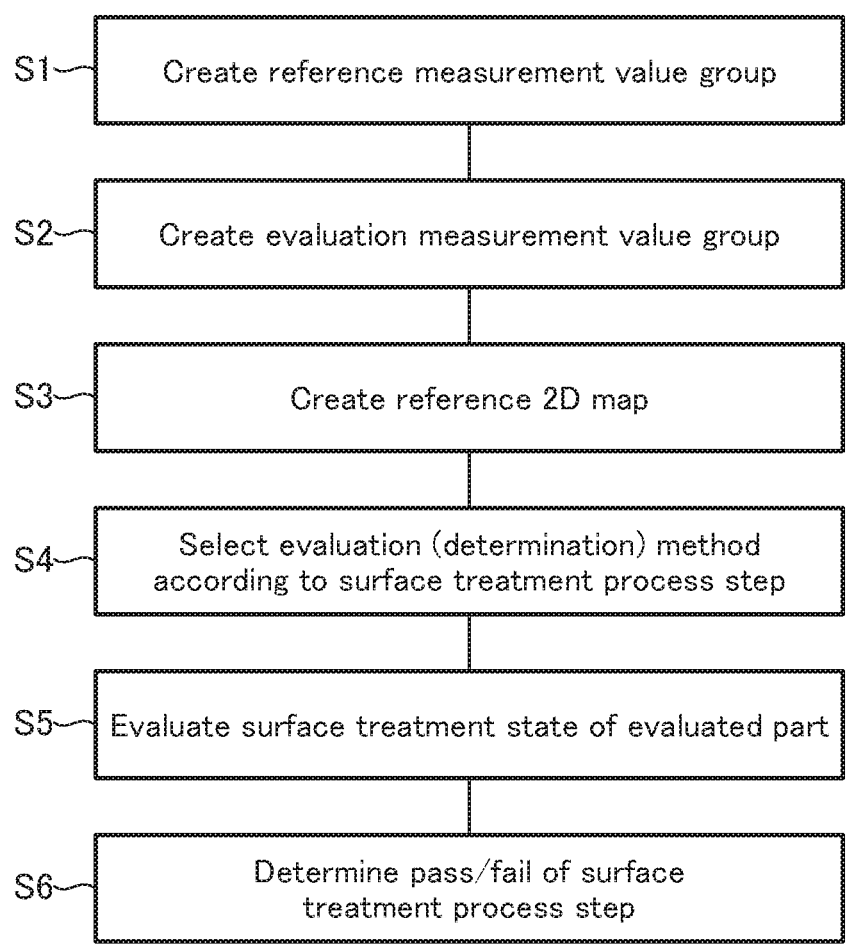
FIG. 3: A flow chart showing a surface property evaluation method.

As shown in FIG. 3, in step S1, as a step for creating a reference measurement value group Gγ1, the reference measurement value group Gγ1 is created by using the control means 37 to calculate an impedance ratio γ1 ($Z_1/Z_0$) for the comparative sample impedance $Z_0$ and a reference sample impedance $Z_1$ at multiple frequencies.

Here it is preferable for the comparative sample impedance $Z_0$ to average measurement results for 10 or more comparative samples T1 at each frequency, then, using those average values, to adopt a reference value by calculating an impedance ratio γ1 for each frequency. Also, for the impedance of the reference samples T2, it is preferable to measure the impedance $Z_1$ of 30 or more good samples to calculate the standard deviation used to set the threshold value in the evaluation method described below.

In step S2, as a step for creating an evaluation measurement value group Gγ2, the evaluation measurement value group Gγ2 is created by calculating an impedance ratio γ2 ($Z_2/Z_0$) of the impedance $Z_2$ of the test subject product T3 at the same multiple frequencies as the reference measurement value group relative to the comparative sample impedance $Z_0$ at each frequency.

Voltage drift caused by changes in measurement environment (temperature, humidity, etc.) can be reduced by using the impedance ratio 71, 72 in evaluating surface properties. In addition, the accuracy of the evaluation of the surface property is improved, since it is possible to extract changes in the electromagnetic properties of the test piece T caused by surface treatment only. Furthermore, compared to the difference in impedance ratios, changes can be more noticeably detected, so surface treatment evaluation accuracy is improved.

In the next step S3, a reference 2D map is created, displaying an impedance ratio γ1 relative to depth from the surface of the reference sample T2, based on reference measurement value group Gγ1. The reference 2D map calculates depths from the surface of the reference sample T2 based on frequency and, using this as the horizontal axis, plots the corresponding impedance ratio γ1. By creating a calibration curve showing the relationship between frequency and depth from surface using the formula below, the relationship between frequency and depth from the reference sample surface can be calculated from this calibration curve.

$$y = \kappa \frac{1}{\sqrt{\pi x \mu \sigma}}$$

y: Penetration depth of AC magnetism (μm)

k: Correction coefficient x: AC magnetism frequency (Hz)

μ: Steel permeability (H/m)

σ: Steel conductivity (S/m)

When the frequency is high, a signal reflecting the surface treatment state near the surface is obtained, and when frequency is low, a signal reflecting the surface treatment state in a deeper region is obtained. The correction coefficient k in the above formula is a fluctuating value affected by the test piece T shape (e.g., the volume of the test piece T) or properties (e.g., the presence or absence of heat treatment as a previous step), or conditions of the SP treatment (e.g., shot particle diameter, hardness, blast time, blast pressure), and is experimentally calculated in advance.

Here, the reference 2D map can also be created by plotting the impedance ratio against frequency.

Figure 4:
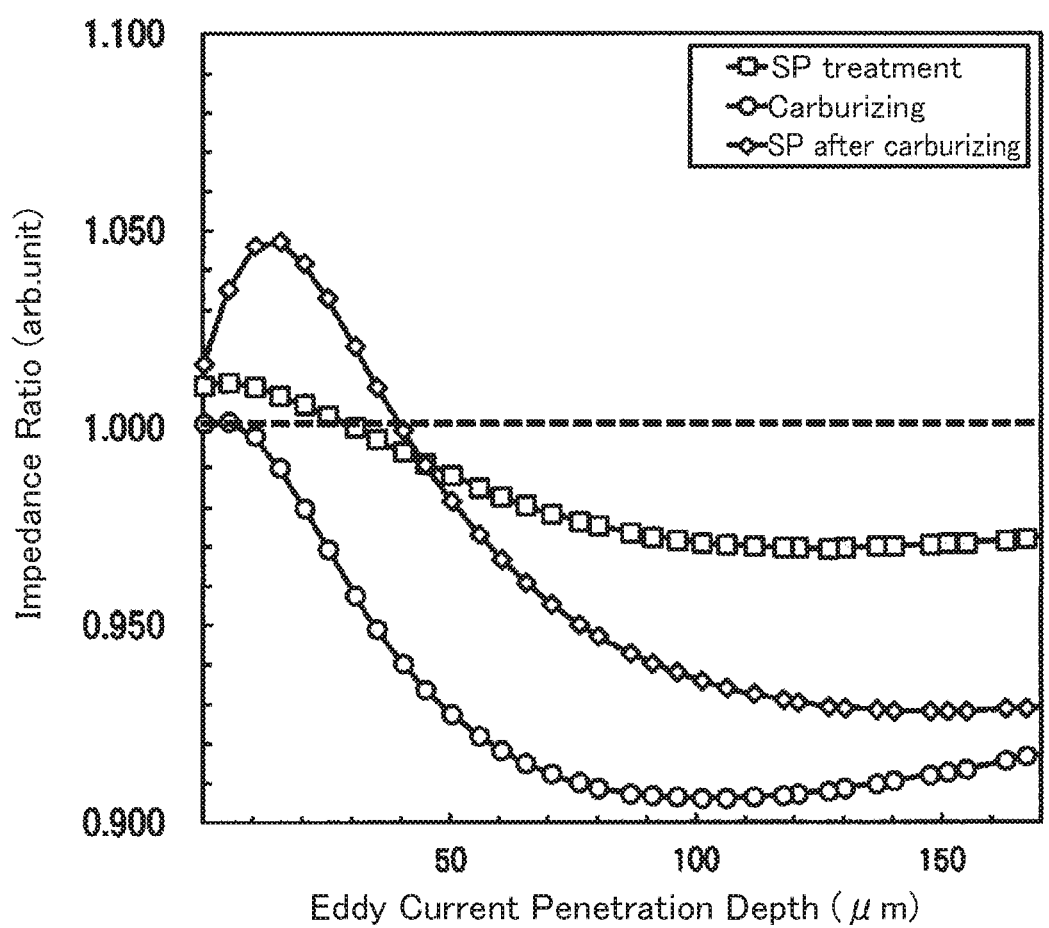
FIG. 4: A 2D map of impedance in a carburized sample, an SP-treated sample, and a post-carburized SP-treated sample wherein SP-treatment was performed after carburization.

Below we show an example of an impedance ratio reference 2D map. FIG. 4 shows a reference 2D map of impedance ratios in a carburized sample, an SP-treated sample, and a SP-treated sample which was SP-treated after carburization treatment.

Shot peening was performed by blasting shot (all made by SINTOKOGIO, Ltd.) with an average particle diameter of 50 μm to 1000 μm toward a carburization hardened chrome-molybdenum steel (40 mm×30 mm) using a shot peening machine (manufactured by SHINTOKOGIO, Ltd.) so that coverage was 300% at a blast pressure of 0.3 MPa. This chrome-molybdenum steel treated with shot peening was used as the test piece T. 10 kHz to 20 MHz was used as the AC current frequency (working frequency). Also, the AC magnetism penetration depth was calculated from the working frequency using the above-described calibration curve.

If the impedance ratio exceeds 1 in the reference 2D map of the impedance ratio, this means permeability is increased compared to the untreated product, and if the impedance ratio is less than 1, permeability is decreased compared to the untreated product.

Since the factors affecting impedance and the depth affecting surface treatments vary depending on the surface treatment step, the tendency of the impact of the impedance ratio between untreated product and surface treated product differs between surface treatment steps. The factors affecting impedance differ, such as structural change in carburizing treatment, martensitic transformation in SP treatment, and residual stress caused by imparting of strain, etc. Further, the depth affected by the surface treatment is approximately several hundred μm in carburized samples, whereas it is approximately several tens of μm in SP-treated samples, so it is in a shallower region near the surface in SP-treated samples.

In carburized samples, the impedance ratio is 1 near the surface, and tends to decrease greatly as distance from the surface increases.

In SP-treated samples, the impedance ratio exceeds 1 in the vicinity of the surface. A gradual decrease is shown as the distance from the surface increases. Also, the degree of decrease in the impedance ratio is smaller compared to carburized samples.

In post-carburized SP-treated samples, the impedance ratio exceeds 1 near the surface, and increases up to about 15 μm from the surface, then decreases and exhibits a tendency to become 1 or less at approximately 40 μm. Thus when there are multiple surface treatment steps and carburizing and SP treatment are combined, the reference 2D map of the impedance ratios describes a curve with a local maximum value.

A pass/fail determination of surface treatment state is made by the control means 37 using the obtained reference 2D map and the evaluation measurement value group Gγ2.

In step S4, an evaluation reference is selected according to the surface treatment process. As the evaluation criteria, three types of criteria are used: the area width criterion, the peak criterion, and the integral area criterion using the reference 2D map and the evaluation measurement value group, and an evaluation criterion is selected from among these.

The area width criterion sets an allowable range W1 for the impedance ratio at each frequency from the reference measurement value group Gγ1 and compares said allowable range with the evaluation measurement value group Gγ2 impedance ratio γ2 to evaluate the surface treatment state of the test piece T.

An average value and standard deviation a are calculated relative to the impedance ratio γ1 for each frequency, and the above allowable range is set based on those values. For example, in accordance with the quality control range, set a standard deviation multiple N, and set as a threshold group the value of N times the standard deviation a relative to the average value γ1 of the impedance ratio γ2.

Here the allowable range W1 may have a different value at each depth. Also, the allowable range W1 may be set at a constant width above and below the average value, or may be set to a threshold width which differs above and below a specific frequency.

Figure 5A:
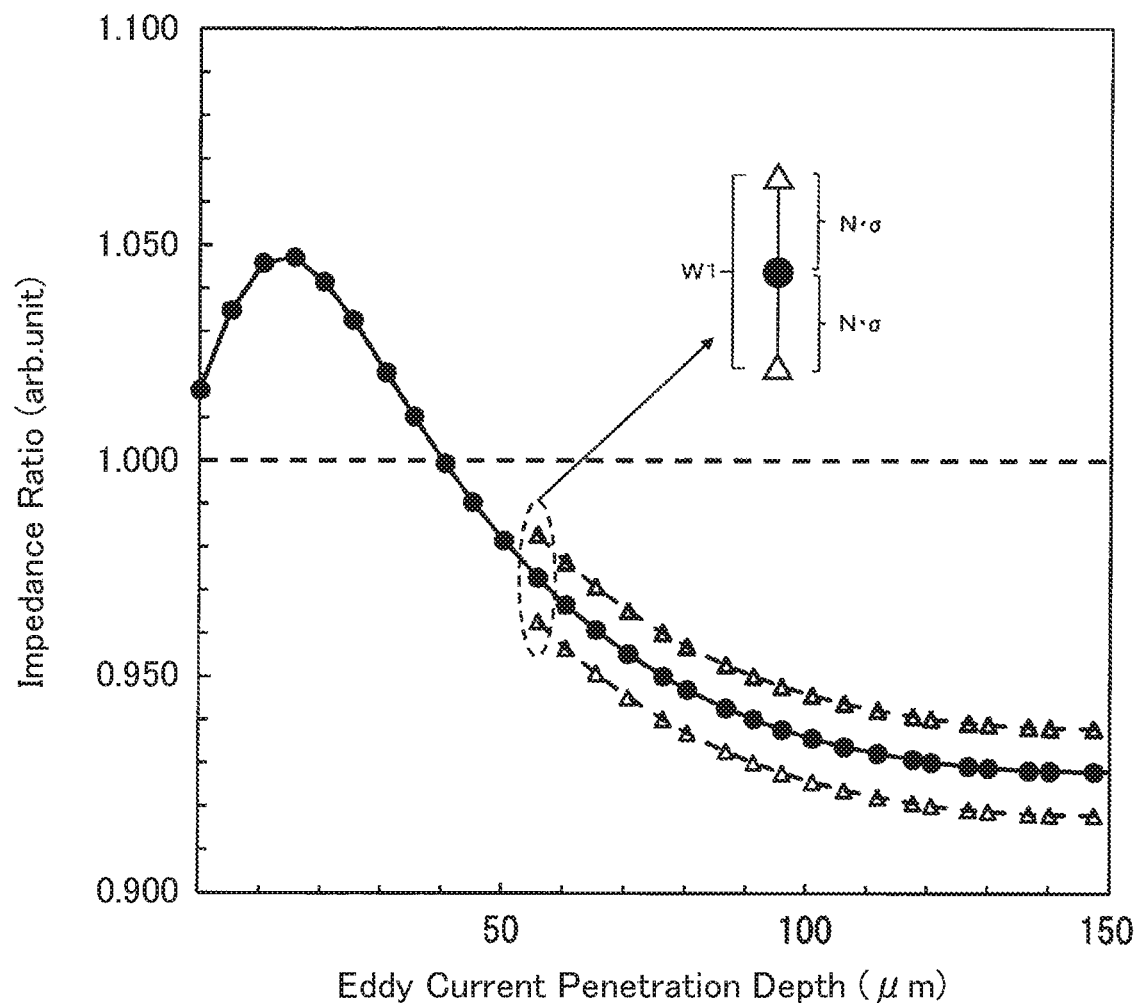
FIG. 5A: A diagram explaining a method for evaluating the surface treatment state of the test subject product using an area width criterion in the determination step.
Figure 5B:
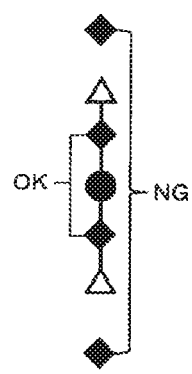
FIG. 5B: A diagram explaining an allowable evaluation range using an area width criterion.

FIG. 5A shows a reference 2D map displaying the allowable range W1. The impedance ratio γ1 curve is drawn by the average value of the impedance ratio γ1 at each frequency, and an allowable range W1 is set for each depth corresponding to the frequencies at which the impedance ratio γ1 is calculated. The width of the allowable range W1 is indicated by Δ in FIG. 5A. As shown in FIG. 5B, for each depth an impedance ratio γ2 (♦ in the figure) is compared to the curve of impedance ratio γ1. I.e., a determination of OK is made if the impedance ratio γ2 (♦ in the figure) is within the allowable range W1 (Δ in the figure) set for the frequency (penetration depth), and a determination of NG (no good) is made if outside that. In instances where all the impedance ratios γ2 fall within the allowable range W1 for each depth, an evaluation is made by control means 37 that the surface treatment state is good. On the other hand, in instances where the impedance ratio γ2 does not fall within the allowable range W1, an evaluation is made by the control means 37 that the surface treatment state is not good.

The peak criterion sets an allowable range for the position of the extremum M (peak position) of the impedance ratio from the reference measurement value group Gγ1, and compares said allowable range and the position of the impedance ratio γ2 extremum to evaluate the surface treatment state of the test piece T.

Figure 6A:
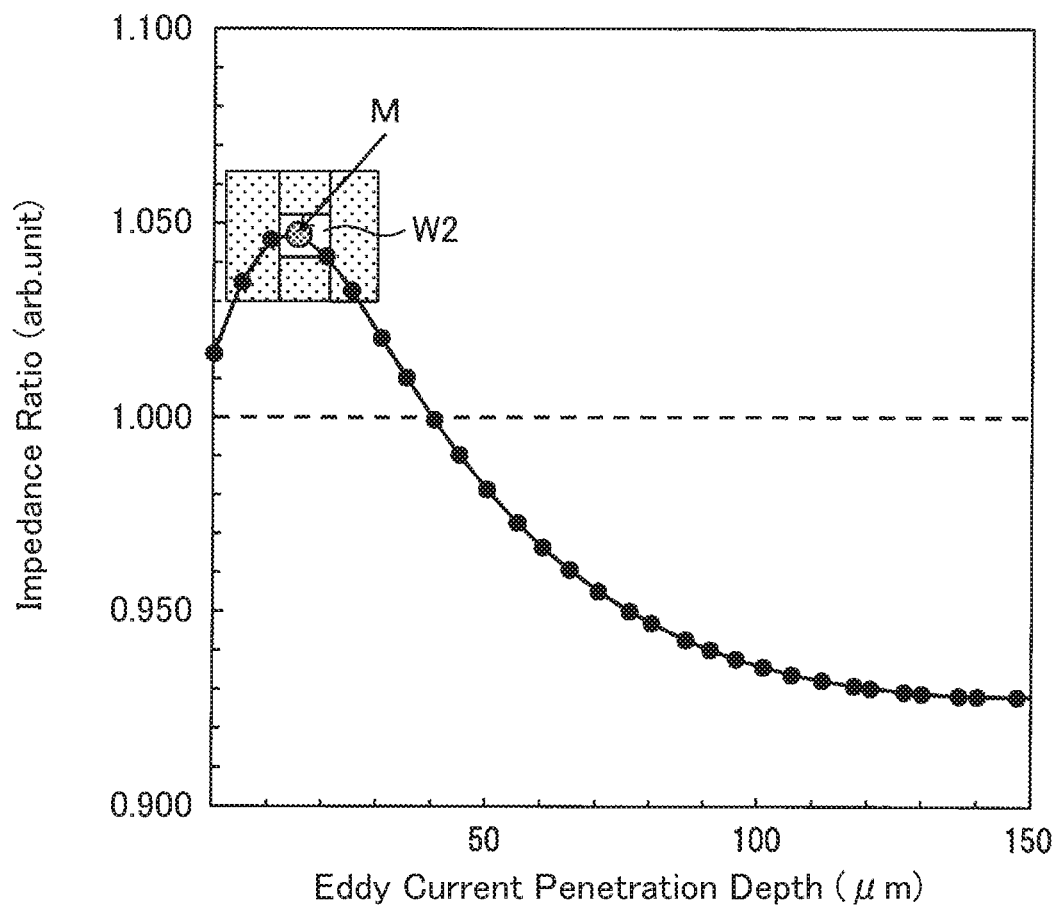
FIG. 6A: A diagram explaining a method for evaluating the surface treatment state of the test subject product using a peak criterion in the determination step.

As shown in FIG. 6A, when the surface treatment is good in the reference 2D map, the range in which an extremum can exist is set as the allowable range W2. The allowable range W2 is set (FIG. 6B) as a rectangular area surrounded by the allowable range of depth and allowable range of impedance ratios determined based on the standard deviation of the depth and the standard deviation of the impedance ratio, consistent with the quality control range.

Figure 6B:
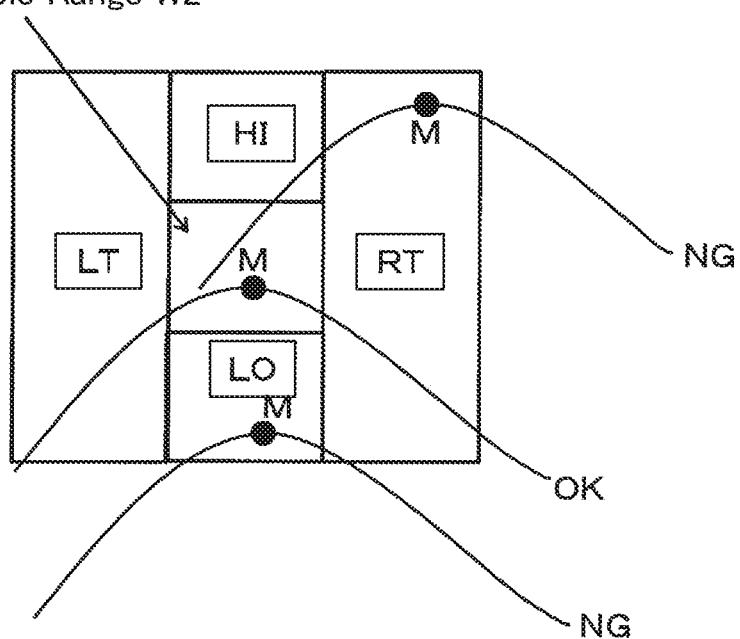
FIG. 6B: A diagram explaining allowable evaluation range using a peak criterion.

As shown in FIG. 6B, when the extremum M of the impedance ratio γ2 exists within this rectangular area (allowable range W2), the surface treatment state is evaluated as good by the control means 37. On the other hand, if the extremum M of the impedance ratio γ2 does not fall within this rectangular area, the control means 37 evaluates that the surface treatment state is not good.

Here, a 2D map (distribution of impedance ratios) having such extrema near the surface of the test piece T is such that a noticeable extremum appears due to the action of the SP treatment close to the surface of the test piece T, and can thus be favorably used to make a pass/fail determination of SP treatment. Note that such extrema can also be found in surface treatments other than by SP.

FIG. 7 shows changes in the impedance ratio due to the diameter of shot used in SP treatment. As described above, the SP processing using level 4 shot (manufactured by SINTOKOGIO. Ltd.) with an average particle diameter of 50 μm to 800 μm was carried out on carburized and hardened chrome molybdenum steel (φ 40 mm×30 mm) as the test piece T. 10 kHz to 20 MHz was used as the AC current frequency (working frequency). Also, the AC magnetism penetration depth was calculated from the working frequency using the above-described calibration curve. As the shot diameter increased, extrema (maximum values) appeared in the direction of depth from the surface, and those values also increased.

Note that in some cases minimum values also appeared as extrema, depending on the steel type and the surface treatment step.

The area below, shown in FIG. 6B, may be set as the area adjacent to the rectangular area.

HI: Area in which coordinates of the extrema of the impedance ratio γ2 satisfy the allowable range of depth, but impedance ratio is high LO: Area in which coordinates of the extrema of the impedance ratio γ2 satisfy the allowable range of depth, but impedance ratio is low LT: Area in which coordinates of the extrema of the impedance ratio γ are outside the allowable range on the shallow side of the depth range RT: Area in which coordinates of the extrema of the impedance ratio γ are outside the allowable range on the deep side of the depth range Considering the tendency shown in FIG. 7, the SP treatment state can be grasped based on the above-described region in which the extremum of the impedance ratio γ2 exists.

HI: detection of over peening when blast time is long and SP treatment quantity is large.

LO: detection of insufficient peening, as projection time is short, and SP treatment quantity is low.

LT: detection of shot wear when shot diameter is small and treatment range is closer to the outermost surface, or detection of mixing of different particle sizes when shot smaller than specification was used.

RT: detection of mixing of different particle sizes when shot larger than specification is used.

Next, an allowable range W3 for the integral value of impedance ratios in a frequency preset from the reference measurement value group Gγ1 is set, and the surface of the test piece T is evaluated by comparing said allowable range W3 to the integrated value of the impedance γ2 in said frequency range.

Specifically, as shown in FIG. 8, an area S surrounded by the curve of the impedance ratio γ2 and by the straight line showing impedance ratio=a predetermined value is calculated. In the example shown in FIG. 8, the area (hereinafter referred to as "integral area S") of the region surrounded by the curve (evaluation 2D map) of the impedance ratio γ2 including the extremum M and the straight line of the impedance ratio=1 is calculated. I.e., in the FIG. 8 example, the curve of the impedance ratio γ2 takes a maximum value M at the position where the eddy current penetration depth is =approximately 20 μm, and at the position where the eddy current penetration depth is =about 40 μm, there is a decline down to where the impedance ratio γ2 is =1. Therefore the integral area of S in FIG. 8 can be obtained by integrating the value obtained by subtracting 1 from the impedance ratio γ2 over an eddy current penetration depth range of 0 to approximately 40 μm.

The integral area S is calculated by calculating the average value of integral area S similarly calculated from multiple reference 2D maps (impedance ratio γ1 maps) and the standard deviation thereof, and is preset according to the quality control range. Next, if the integral area S calculated for the curve (impedance distribution) of the impedance ratio γ2 obtained for the test subject product T3 is within the allowable range W3, then the surface treatment state of the test subject product T3 is evaluated as good.

Features of each evaluation method are shown below.

The area width criterion enables a determination across a broad range in the depth direction. It can thus be favorably used to determine whether appropriate treatment has been performed to a predetermined depth in a surface treatment process such as a carburizing treatment in which modification is performed down to a deep range.

The peak criterion is determined using the coordinates of the extremum of the impedance ratio γ2 in the evaluation 2D map, and can therefore be favorably used for a pass/fail determination in surface treatments, especially SP treatments, which present an evaluation 2D map with extrema.

The integral area criterion is able to detect minute differences between the evaluation 2D map and the reference 2D map for which determination is difficult using the area width criterion or the peak criterion. Also, by calculating the integral area S, which is obtained by integrating over a predetermined depth range, the impedance ratio γ2, which includes a depth range and extrema, can be favorably used to determine pass/fail for SP treatment.

In step S5, as a process for evaluating the surface treatment state of the test subject product T3, a predetermined evaluation criterion set based on reference measurement value group Gγ1 is compared to an evaluation measurement value group Gγ2 to evaluate the surface treatment state of the test subject product T3. At least one of the area width criterion, peak criterion, or integral area criterion is applied to the evaluation 2D map obtained based on the evaluation measurement value group Gγ2 to evaluate the surface treatment state of the test subject product T3. Surface treatment state evaluation results are output to the display 38 and displayed. It is possible to display only a pass/fail result on the display 38, or to issue a warning when a fail determination is made.

In addition, in step S6, as described below, a pass/fail determination is made of the surface treatment process applied to the test subject product T3.

The steps above enable the selection, based on surface treatment process, of an evaluation method for evaluating the surface treatment state considering the depth direction from the surface of the test piece T.

In step S4, taking advantage of the features of each determination method, multiple evaluation methods can be adopted according to the surface treatment process applied to the test subject product T3.

For example, as shown in FIG. 9, a determination method may be adopted whereby an integral area criterion is used in the region where the impedance ratio is 1 or greater for the test subject product T3 on which SP treatment is performed after carburization, and an area width criterion is used in regions of greater depth. By so doing, determination of pass/fail of the SP treatment step can be performed by the integral area criterion in the shallow region, and determination of pass/fail of the carburization treatment step in deeper regions can be performed by the area width criterion, so that it is unnecessary to evaluate a test piece T after the carburization, and evaluation of multiple surface treatment steps can be performed in a single iteration by evaluating the test piece T after all surface treatments are completed.

Also, an evaluation method may be employed in which evaluation of the test subject product T3 treated with SP after carburization is performed by the peak criterion on shallow regions and by the area width criterion on deep regions. By so doing, a pass/fail determination of the SP treatment step having extrema close to the surface can be performed by the peak criterion in the shallow region, and a pass/fail determination of the carburization treatment step in deeper regions can be performed by the area width criterion, making it unnecessary to evaluate a test piece T after carburization, and evaluation of multiple surface treatment steps can be performed in a single iteration by evaluating the test piece T after all surface treatments are completed.

Other examples in which multiple surface treatment steps are performed are shown in the order in which surface treatment is performed.

Carburization quenching and tempering→SP→polishing
Carburization quenching and tempering→SP (first stage) →SP (second stage) polishing
Thermal nitriding→SP→low temperature annealing As noted above, when multiple surface treatment steps are performed, it is possible to evaluate the test subject product T3 in a manner which determines a surface treatment state pass/fail for each process step using a single measurement.

Here, when the multiple surface treatment steps are performed, pass/fail of the surface treatment state in each step can be evaluated by a single determination method, for example, the area width criterion alone.

When the multiple surface treatment steps are performed, a pass/fail determination of the surface treatment steps is made in step S6 based on the results of the surface treatment state evaluations. The determination results are output to the display device 38 and displayed. On the display device 38, it is possible to display a pass/fail result only, or to issue a warning when a fail determination is made.

As in step S3, an evaluation 2D map displaying the impedance ratio γ2 relative to the depth from the surface of the test subject product T3 can be created based on the evaluation measurement value group Gγ2. Once the evaluation 2D map is created, an evaluation result pass/fail, the degree thereof, and so forth can be easily visually understood by comparison with the reference 2D map. Furthermore, the surface treatment state in the depth direction can be visually understood by the trajectory of the impedance ratio γ2 shown in the evaluation 2D map.

Figure 10:
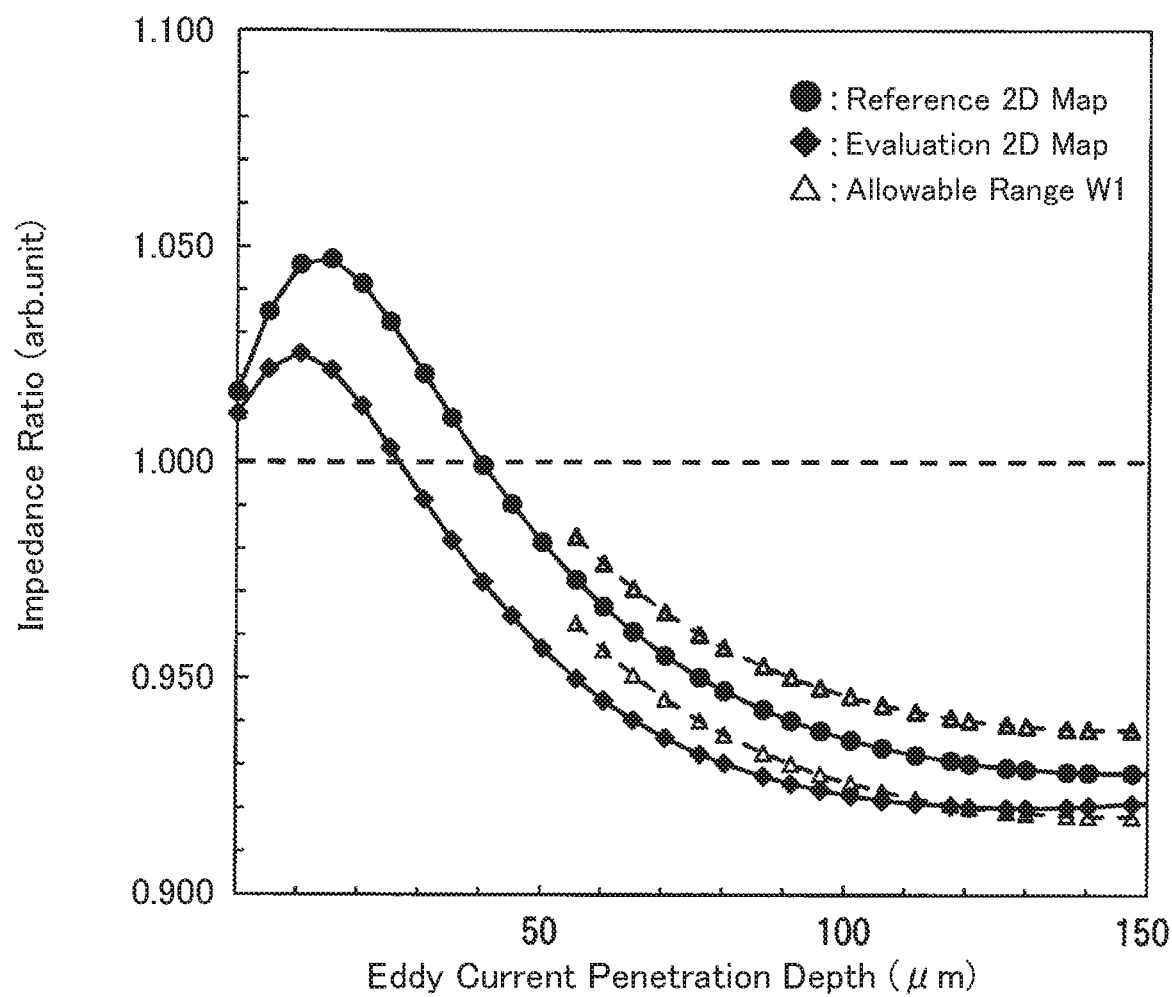
FIG. 10: An explanatory diagram of the surface treatment state evaluation method of the test subject product performed by an area width criterion using a reference 2D map and an evaluation 2D map.

For example, when making a determination using the area width criterion, it is possible, as shown in FIG. 10, to superimpose the reference 2D map and the evaluation 2D map so as to make the determination by comparison with the allowable range W1.

(Surface Property Evaluation System)

In the surface property evaluation system 1, a surface property evaluation system can be connected or built into a surface treatment apparatus to constitute a surface treatment evaluation system for transmitting evaluation results regarding the surface treatment state of the test subject product T3.

Figure 11:
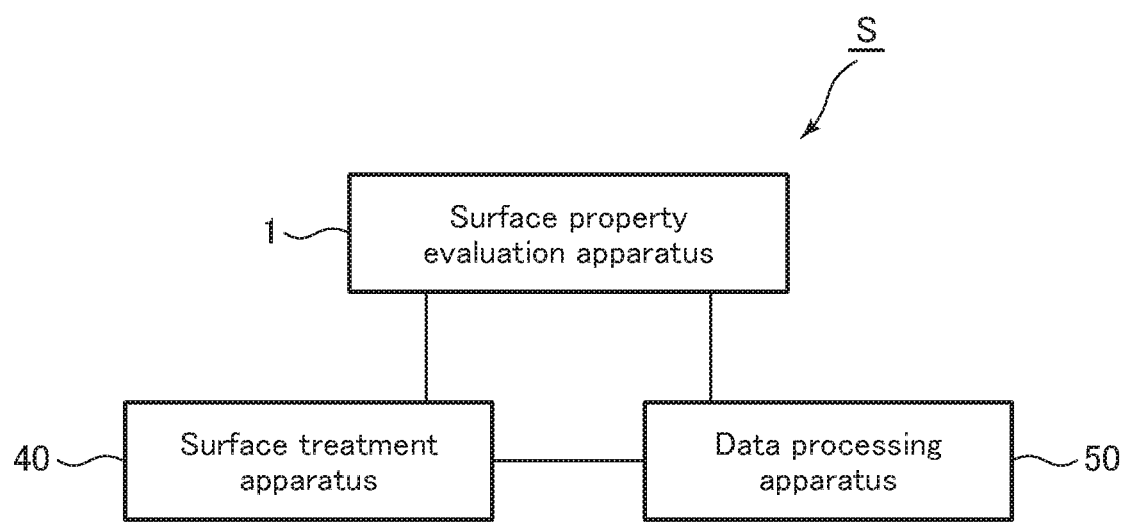
FIG. 11: A block diagram showing the constitution of a surface treatment evaluation system.

FIG. 11 shows an example of a surface property evaluation system S. The surface property evaluation system S comprises a surface property evaluation apparatus 1, a surface treatment apparatus 40, and a data processing apparatus 50. The surface property evaluation system S is capable of controlling the surface treatment apparatus 40 based on evaluation results for the surface treatment state of the test subject product T3. Here, control of the surface treatment apparatus 40 is performed by either the surface treatment apparatus 40 or the data processing apparatus 50.

When there are multiple surface treatment steps, it is possible to select either then entirety of the surface treatment apparatus 40 performing said surface treatment (heat treatment machinery, multiple shot peening machines, etc.), or to select a portion thereof, and connect or build the same into the surface property evaluation apparatus 1 so as to constitute a surface property evaluation system from the surface property evaluation apparatus 1 and the selected surface treatment apparatus.

In the surface property evaluation system S, a determination can be made of an anomaly in a surface treatment step by any of the surface treatment apparatuses 40 among multiply selected surface treatment apparatuses, based on the evaluation results for the surface treatment state of the test subject product T3 in the surface property evaluation apparatus 1. Here, said determination may be performed by either the surface treatment apparatus 40 or the data processing apparatus 50.

The surface property evaluation system S can output the evaluation result from the surface property evaluation apparatus 1 to a surface treatment apparatus 40 such as a shot peening apparatus. This enables surface treatment conditions to be varied based on evaluation results, thereby reducing the occurrence of defective samples. Changes in these surface treatment conditions may be made manually by operators based on evaluation results, or may be made automatically by outputting signals correcting or changing surface treatment conditions to the surface treatment apparatus 40 based on the evaluation results.

The surface property evaluation system S can also be constituted to connect to at least one or more of the surface treatment apparatuses 40, recording the results of the surface treatment state of the test subject product T3 and playing these back as needed. This stored data may be used for process control purposes.

In addition, the surface property evaluation system S can correlate the treatment conditions in the connected surface treatment apparatus 40 with evaluation results measured by the surface property evaluation apparatus 1 and cause these to be recorded in the data processing apparatus 50. Since surface treatment conditions and evaluation results for each test subject product T3 are correlated and recorded, it is possible when a failure occurs in a later step, for example, to confirm the history of the prior surface treatment step and identify in which step the problem occurred. Since these results can be reflected in each process, it becomes possible to manufacture products with higher reliability.

(Effect of the Embodiment)

The surface property evaluation method and the surface property evaluation apparatus 1 of the present invention comprise an impedance distribution acquisition step for acquiring an impedance distribution in the depth direction of a test piece T, and an impedance distribution analysis step for evaluating the surface treatment state in the depth direction based on an impedance distribution found by the impedance distribution acquisition step; and an evaluation of the surface treatment state with consideration of the depth direction from the surface of the test subject product T3 can be performed by comparing a reference measurement value group Gγ1, which calculates the impedance ratio γ1 at each frequency for the impedance of the comparative samples T1 and the reference samples T2 at multiple frequencies in the impedance distribution analysis step, to an evaluation measurement value group Gγ2, which calculates an impedance ratio γ1 between impedance of the test subject product T3 at the same frequencies as for the reference measurement value group Gγ1, and the impedance of the comparative samples T1 at each frequency. Since evaluation is done by selecting a criterion suited to the surface treatment step from among the area width criterion, the peak criterion, and the integral area criterion as the evaluation method, a higher accuracy of evaluation can be performed. Also, by selecting an evaluation method suited to the surface treatment process in accordance with depth from the surface of the test subject product T3, a separate pass/fail evaluation for each process step can be made of the surface treatment state in each process by a single measurement of the test subject product T3.

Using the surface property evaluation system of the present invention, a surface property evaluation apparatus 1 can be connected or built into a surface treatment apparatus 40, and the evaluation results for the surface treatment state of test subject product T3 can be transmitted. A surface property evaluation system can control the surface treatment apparatus 40 based on evaluation results for the surface treatment state of a sample to be evaluated. The surface property evaluation apparatus 1 can determine if there is an anomaly in a surface treatment step by any of the surface treatment apparatuses 40 among multiply selected surface treatment apparatuses 40 based on the evaluation results for the surface treatment state of the test subject product T3.

The invention claimed is:

1. A surface property evaluation method for evaluating surface treatment state of a metal product, comprising:
   - a preparation step for preparing three test pieces consisting of a comparative sample whose surface is not treated, a reference sample whose surface is appropriately treated, and a test subject product for evaluation of performed surface treatment;
   - an impedance distribution acquisition step for acquiring impedance distributions of the three test pieces; and
   - an impedance distribution analysis step for evaluating surface treatment state of the test subject product, based on the impedance distributions acquired in the impedance distribution acquisition step;
   - wherein the impedance distribution acquisition step comprises:
   - a step for disposing each of the three test pieces inside a coil and applying an AC current to the coil to cause an AC magnetism excited by the coil to penetrate into each of the three test pieces;
   - a step for varying the frequency of the AC current applied to the coil, thereby varying a penetration depth of the AC magnetism into each of the three test pieces; and
   - a data acquisition step for acquiring the impedance distribution in a surface of each of the three test pieces by measuring coil impedances at multiple frequencies;
   - wherein the impedance distribution analysis step comprises:
   - a step for calculating an impedance ratio $\gamma 1$ $(Z_1/Z_0)$ at each frequency, wherein the impedance ratio $\gamma 1$ of an impedance $Z_0$ of the comparative sample and an impedance $Z_1$ of the reference sample is acquired at each of the multiple frequencies in the data acquisition step to create a reference measurement value group $G\gamma 1$;
   - a step for calculating at each frequency for the same multiple frequencies as in the reference measurement value group $G\gamma 1$ an impedance ratio $\gamma 2$ $(Z_2/Z_0)$, wherein the impedance ratio $\gamma 2$ of an impedance $Z_2$ of the test subject product and the impedance $Z_0$ of the comparative sample is acquired in the data acquisition step to create an evaluation measurement value group $G\gamma^2$; and
   - a step for evaluating the surface treatment state of the test subject product by comparing certain evaluation criteria, set based on the reference measurement value group $G\gamma 1$, with the evaluation measurement value group $G\gamma 2$;
   - wherein the evaluation criteria are selected from among:
   - an area width criterion in which the surface treatment state of the test subject product is evaluated by setting an allowable impedance ratio range at each frequency based on the impedance ratio $\gamma 1$ at each frequency of the reference measurement value group $G\gamma 1$ and comparing said allowable impedance ratio range to the impedance ratio $\gamma 2$;
   - a peak criterion in which the surface treatment state of the test subject product is evaluated by setting an allowable peak position range based on the peak position of the reference measurement value group $G\gamma 1$ relative to frequency and comparing said allowable peak position range to the peak position in the impedance ratio $\gamma 2$; and
   - an integral area criterion in which the surface treatment state of the test subject product is evaluated by setting an allowable integral value range based on the integral value of the impedance ratio $\gamma 1$ of the reference measurement value group $G\gamma 1$ in a predetermined frequency range, and comparing said allowable integral value range to the integral value of the impedance ratio $\gamma 2$ in said frequency range.

2. The surface property evaluation method of claim 1, wherein the impedance distribution analysis step comprises a step for calculating the penetration depth of the AC magnetism into the test subject product based on the frequency of AC current applied to the coil, and the surface treatment state is evaluated by respectively producing a reference 2D map displaying the impedance ratio T1 relative to depth from the surface for the reference sample based on the reference measurement value group $G\gamma 1$, and an evaluation 2D map displaying the impedance ratio $\gamma 2$ relative to depth from the surface of the sample to be evaluated based on the evaluation measurement value group $G\gamma^2$.

3. The surface treatment evaluation method of claim 1, wherein in the impedance distribution analysis step, when evaluating the surface treatment state of the test subject product to which multiple surface treatments have been applied, different evaluation criteria are selected according to the depth from the surface of the test subject product.

4. The surface property evaluation method of claim 1, wherein when the surface treatment applied to the test subject product includes shot peening, the peak criterion or the integral area criterion is selected to evaluate the surface treatment close to the surface of the test subject product.

5. The surface property evaluation method of claim 4, wherein in the impedance distribution analysis step, the state of surface treatment by shot peening is evaluated.

6. The surface property evaluation method set forth in claim 1, wherein the allowable ranges for the area width criterion, the peak criterion, and the integral area criterion are set based on the variability of multiple reference measurement value groups $G\gamma 1$.

7. A surface property evaluation apparatus for evaluating surface treatment of a metal product, comprising:
   - an oscillator comprising an AC power supply and a variable frequency circuit capable of varying a frequency of AC current output by the AC power supply;
   - a detector connected to the oscillator, comprising a coil for exciting AC magnetism by the AC current applied from the variable frequency circuit, for causing the AC magnetism to penetrate each of three test pieces, wherein the three test pieces consist of a comparative sample whose surface is not treated, a reference sample whose surface is appropriately treated, and a test subject product for evaluation of performed surface treatment;
   - a measurement instrument, connected to the variable frequency circuit and the detector, for acquiring an impedance distribution for each of the three test pieces; and an evaluation device that evaluates the surface treatment state of the test subject product based on the impedance distribution acquired for the test subject product, wherein the evaluation device is configured to implement:

a preparation step for preparing the three test pieces;

an impedance distribution acquisition step for acquiring impedance distributions of each of the three test pieces; and an impedance distribution analysis step for evaluating surface treatment state of the test subject product, based on the impedance distributions acquired in the impedance distribution acquisition step;

wherein the impedance distribution acquisition step comprises:

a step for disposing each of the three test pieces inside a coil and applying an AC current to the coil to cause an AC magnetism excited by the coil to penetrate into each of the three test pieces;

a step for varying the frequency of the AC current applied to the coil, thereby varying a penetration depth of the AC magnetism into each of the three test pieces; and a data acquisition step for acquiring the impedance distribution in a surface of each of the three test pieces by measuring coil impedances at multiple frequencies;

wherein the impedance distribution analysis step comprises:

a step for calculating an impedance ratio $\gamma 1$ ($Z_1/Z_0$) at each frequency, wherein the impedance ratio $\gamma 1$ of an impedance $Z_0$ of the comparative sample and an impedance $Z_1$ of the reference sample is acquired at each of the multiple frequencies in the data acquisition step to create a reference measurement value group $G\gamma 1$;

a step for calculating at each frequency for the same multiple frequencies as in the reference measurement value group $G\gamma 1$ an impedance ratio $\gamma 2$ ($Z_2/Z_0$), wherein the impedance ratio $\gamma 2$ of an impedance $Z_2$ of the test subject product and the impedance $Z_0$ of the comparative sample is acquired in the data acquisition step to create an evaluation measurement value group $G\gamma 2$; and a step for evaluating the surface treatment state of the test subject product by comparing certain evaluation criteria, set based on the reference measurement value group $G\gamma 1$, with the evaluation measurement value group $G\gamma 2$;

wherein the evaluation criteria are selected from among:

an area width criterion in which the surface treatment state of the test subject product is evaluated by setting an allowable impedance ratio range at each frequency based on the impedance ratio $\gamma 1$ at each frequency of the reference measurement value group $G\gamma 1$ and comparing said allowable impedance ratio range to the impedance ratio $\gamma 2$;

a peak criterion in which the surface treatment state of the test subject product is evaluated by setting an allowable peak position range based on the peak position of the reference measurement value group $G\gamma 1$ relative to frequency and comparing said allowable peak position range to the peak position in the impedance ratio $\gamma 2$; and an integral area criterion in which the surface treatment state of the test subject product is evaluated by setting an allowable integral value range based on the integral value of the impedance ratio $\gamma 1$ of the reference measurement value group $G\gamma 1$ in a predetermined frequency range, and comparing said allowable integral value range to the integral value of the impedance ratio $\gamma 2$ in said frequency range.

8. A surface property evaluation system comprising:

the surface property evaluation apparatus set forth in claim 7, and one or multiple surface treatment apparatuses connected to the surface property evaluation apparatus;

whereby the surface property evaluation apparatus is capable of transmitting evaluation results for the surface treatment state of the test subject product to a selected surface treatment apparatus.

9. The surface property evaluation system of claim 8, wherein the surface property evaluation apparatus is configured to control the selected surface treatment apparatus.

10. The surface property evaluation system of claim 8, wherein the test subject product has been subjected to multiple surface treatments by multiple surface treatment apparatuses, and the surface property evaluation apparatus determines which one of the multiple surface treatment apparatuses applies a surface treatment anomaly.

11. A surface property evaluation system comprising the surface property evaluation apparatus of claim 7, wherein the surface property evaluation apparatus is configured to record and play back evaluation results for the surface treatment state of the test subject product.

12. The surface property evaluation system of claim 11, further comprising one or multiple surface treatment apparatuses connected to the surface treatment evaluation apparatus, wherein the surface treatment evaluation apparatus is configured to record surface treatment conditions for a surface treatment apparatus used to surface treat the test subject product, in association with evaluation results for the test subject product.

* * * * *